(12) United States Patent
Oberle et al.

(10) Patent No.: US 8,789,524 B2
(45) Date of Patent: Jul. 29, 2014

(54) PULSE WIDTH MODULATED MEDICAL GAS CONCENTRATION CONTROL

(75) Inventors: Michael D. Oberle, Middleton, WI (US); John Carl Probert, Madison, WI (US)

(73) Assignee: General Electric Company, Schenectady, NY (US)

(*) Notice: Subject to any disclaimer, the term of this patent is extended or adjusted under 35 U.S.C. 154(b) by 1623 days.

(21) Appl. No.: 12/017,815

(22) Filed: Jan. 22, 2008

(65) Prior Publication Data
US 2009/0183737 A1 Jul. 23, 2009

(51) Int. Cl.
*A61M 16/12* (2006.01)
*A61M 16/10* (2006.01)
*A61M 16/20* (2006.01)
*A61M 16/01* (2006.01)

(52) U.S. Cl.
CPC .............. *A61M 16/12* (2013.01); *A61M 16/01* (2013.01); *A61M 2016/1025* (2013.01); *A61M 16/204* (2014.02)
USPC ............. 128/203.25; 128/203.12; 128/200.24

(58) Field of Classification Search
CPC ... A61M 16/00; A61M 16/104; A61M 16/12; A61M 2016/00; A61M 16/10; A61M 2016/1005; A61M 2016/102; A61M 2016/1025; A61M 2016/12; A61M 2016/125; A61M 2016/127; A61M 2202/02; A61M 2202/0208; A61M 16/204; A61M 2016/10
USPC ............. 128/200.24, 203.25, 204.18, 204.21, 128/205.11, 203.12, 203.14, 204.23, 204.22
See application file for complete search history.

(56) References Cited

U.S. PATENT DOCUMENTS

| | | | | |
|---|---|---|---|---|
| 4,903,693 A * | 2/1990 | Yasue | ...................... | 128/203.12 |
| 5,299,568 A * | 4/1994 | Forare et al. | ............. | 128/205.11 |
| 5,383,449 A * | 1/1995 | Forare et al. | ............. | 128/205.11 |
| 5,558,083 A * | 9/1996 | Bathe et al. | ............. | 128/203.12 |
| 5,636,626 A | 6/1997 | Bloch et al. | | |
| 6,089,229 A * | 7/2000 | Bathe et al. | ............. | 128/204.21 |
| 6,142,147 A * | 11/2000 | Head et al. | ............. | 128/204.21 |
| 6,581,599 B1 * | 6/2003 | Stenzler | .................. | 128/204.23 |
| 6,786,217 B2 * | 9/2004 | Stenzler | .................. | 128/204.23 |
| 7,530,353 B2 * | 5/2009 | Choncholas et al. | .... | 128/204.18 |
| 2005/0076907 A1 * | 4/2005 | Stenzler | .................. | 128/204.23 |
| 2005/0103338 A1 | 5/2005 | Bunke et al. | | |
| 2006/0207594 A1 * | 9/2006 | Stenzler et al. | ......... | 128/204.18 |
| 2007/0062532 A1 * | 3/2007 | Choncholas | ............. | 128/204.23 |
| 2007/0062533 A1 * | 3/2007 | Choncholas et al. | .... | 128/204.23 |

FOREIGN PATENT DOCUMENTS

| | | | |
|---|---|---|---|
| EP | 1044700 A2 | 10/2000 | |
| EP | 0894505 B1 | 12/2004 | |

* cited by examiner

*Primary Examiner* — Annette Dixon
(74) *Attorney, Agent, or Firm* — Andrus Intellectual Property Law, LLP (57) ABSTRACT

A specified concentration of oxygen in a medical gas delivered to a patient by a gas delivery system can be achieved through the use of pulse width modulation control of the flows of one or more component medical gases. The flow of component medical gases can be controlled to improve the resolution and concentration range of medical gas delivered at low flow rates. A first flow of a first medical gas is provided and a second flow of a second medical gas is introduced to achieve a desired average medical gas concentration. When the second flow of the second medical gas is introduced, the first flow of the first medical gas is reduced to maintain a desired total medical gas flow rate.

20 Claims, 4 Drawing Sheets

PULSE WIDTH MODULATED MEDICAL GAS CONCENTRATION CONTROL

FIELD OF THE DISCLOSURE

The present disclosure relates to the field of patient respiratory support. More specifically, the present disclosure relates to the control of the concentration of medical gas delivered to a patient receiving ventilation.

BACKGROUND

The delivery of medical gases is a commonly accepted medical practice for the treatment of individuals receiving anesthesia during a medical procedure or surgery.

Commonly, a combination of medical gases are supplied to the patient during gas delivery of ventilation. Since the patient requires oxygen to conduct basic bodily functions, the combined medical gases must include a component of oxygen, usually in a concentration of at least the 21% found in ambient air. Higher concentrations of oxygen may be provided to the patient as a form of respiratory therapy whereby oxygen exchange within the lungs is promoted by a higher oxygen concentration. The medical gases with which the oxygen is combined are often referred to as balance gases as they make up the balance of the medical gas delivered to the patient. While the balance gas may be an inert gas such as nitrogen, or a common gas such as air, CO2, or helium, the balance gas may also include medical gases that further provide a therapeutic effect, such as nitrous oxide ($N_2O$), xenon, or a drug aerosol. Therapeutic balance gases may produce the effect of anesthetizing the patient or reducing the patient's airway resistance.

Effective gas delivery allows a clinician the ability to provide a wide range of oxygen-balance gas concentration mixtures such that the proper therapeutic and respiratory support may be provided to the patient. The medical gases are typically provided via a source of compressed medical gas. The compressed medical gas source may be a permanent source built into the medical care facility with medical gas line attachment points located in each of the rooms of the medical facility. Otherwise, the source of compressed medical gas may be a movable cylinder filled with the compressed medical gas. The anesthesia delivery system, made up of a gas delivery system and mechanical ventilator is typically connected to a pressurized source of each of the required medical gases and the gas delivery subsystem of the anesthesia delivery systems must control and facilitate the mixing of the medical gases to achieve the proper concentration of medical gases and flow rates of medical gas as desired and input by the clinician.

There are at least two electronic medical gas mixing systems that are used in mechanical gas delivery systems. A mixing chamber gas mixing system makes use of a separate mixing chamber wherein the medical gases from the pressurized medical gas sources are accumulated at the desired concentration and at a pressure sufficient to deliver the desired flow of medical gas. This system requires proportional flow valves to be associated with each of the pressurized sources of medical gas as well as the mixing chamber such that the proportion of the medical gases going into the mixing chamber may be controlled and the flow rate of the medical gas out of the mixing chamber may also be controlled. While the mixing chamber mixing system provides good control over the concentration and flow rate of the medical gas provided to the patient, the mixing chamber system suffers from a slow response time to any clinician changes to the medical gas concentration. The mixing chamber must be purged of the old medical gas and refilled at the new desired medical gas concentration each time the medical gas concentration is changed.

An alternative mechanical gas delivery mixing system design eliminates the mixing chamber and the flow valves associated with the mixing chamber and simply relies upon the control of proportional flow valves associated with each of the sources of pressurized medical gas. Flows of the pressurized oxygen and balance gas are controlled such that the total desired flow rate is achieved within the mechanical ventilator as well as the desired resulting concentration. While this mixing system provides a fast response time to clinician changes in the desired medical gas concentration, this system suffers from a resolution problem at the high and low ends of the oxygen concentration. This resolution problem is most pronounced at low flow rates but also applies to some degree at high oxygen concentrations throughout the medical gas flow rate spectrum of the gas delivery system. The resolution problem is due to the fact that the concentration of the medical gas is dependent upon the precise control of the flow rate of each medical gas out of the pressurized medical gas sources, which is limited by minimum flow rates required by the flow sensors.

BRIEF DISCLOSURE

A method of controlling the provision of medical gases to a patient is disclosed herein. The method may include receiving a definition of a desired oxygen concentration, receiving a definition of a desired total medical gas flow rate, and calculating a required proportion of the medical gases to achieve the desired oxygen concentration. The method may further include controlling a first valve to deliver a flow of first medical gas and controlling a second valve to intermittently deliver a flow of a second medical gas such that the average concentration delivered to the patient equals the desired oxygen concentration.

A gas delivery system for delivering at least a first medical gas and a second medical gas to a patient at a determined flow rate and oxygen concentration is further disclosed herein. A first flow valve associated with a first source of a first medical gas regulates the flow of the first medical gas out of the first source. A second flow valve associated with a second source of a second medical gas regulates the flow of the second medical gas out of the second source. A controller communicatively connected to the first and second flow valves controls the first flow valve to produce a flow of the first medical gas in a determined flow rate and intermittently controls the second flow valve to produce a flow of the second medical gas.

DETAILED DISCLOSURE

The delivery of medical gas to a patient requires precise measurement and control of the flows of the component medical gases. The resolution of the measurement and control of the flows of medical gas is dictated by the flow valves and the precision of the flow sensors used in conjunction with each of the medical gas sources. The cost of these electronic components increases exponentially to the increases in component precision. Therefore, a decision at some point must be made balancing the precision of the component versus the resulting cost. A flow monitoring control component with less precision results in decreased resolution of a clinician's control of the medical gas composition delivered to the patient.

Figure 1:
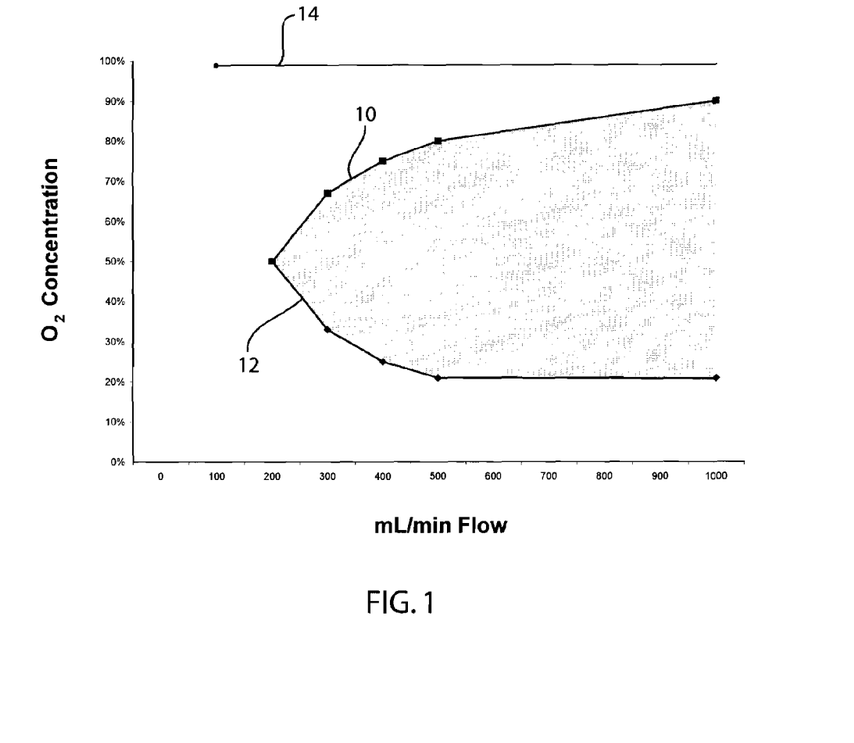
FIG. 1 is a graph depicting an exemplary relationship between medical gas oxygen concentration and total medical gas flow rate delivered to a patient.

FIG. 1 is a graph that represents an example of this resolution problem with respect to a flow sensor that requires a minimum of 100 ml per minute (ml/min) flow rate through the sensor due to the flow accuracy limit of the flow sensor. Any flow sensor will have a threshold minimum flow accuracy limit, for the present example, a sensor with a threshold minimum flow rate of 100 ml/min is described; however, it is understood that flow sensors of other sensitivities may be used. As can be seen by reference to FIG. 1, an upper limit curve 10 and a lower limit curve 12 delineate the oxygen percentage concentrations that may be achieved by the gas delivery system at various total medical gas flow rates. Beginning at a 200 ml/min total medical gas flow rate, a concentration of 50% oxygen and 50% balance gas may be achieved as each medical gas is delivered at the minimum sensor flow rate of 100 ml/min. Any medical gas delivery for lower flow rates between 200 ml/min and 100 ml/min require that 100% oxygen be delivered to the patient as the gas delivery system can deliver solely oxygen as represented by line 14 at any flow rate above the minimum 100 ml/min.

While at a flow rate of 200 ml/min only a 50% oxygen concentration may be achieved, as the total medical gas flow rate increases, the achievable oxygen concentration range also increases. However, even at 300 ml/minute, the achievable oxygen concentration range is still only between 33% and 67% due to the fact that a minimum of 100 ml/min flow of both the oxygen and the balance gas are required. The range of achievable oxygen concentrations increases logarithmically as the 100 ml/minute minimum flow rate for each of the medical gases becomes a smaller percentage of the total flow of medical gas. The lower concentration curve 12 is further limited in that minimum clinical oxygen concentration limits must be delivered to the patient, such that the patient is not delivered medical gas with too low of an oxygen concentration.

Therefore, it can be seen that a wide range of oxygen concentrations may be provided to a patient at the vast majority of medical gas flow rates (2 L/min-15 L/min) delivered in a clinical setting. However, at low total medical gas flow rates (especially <1 L/min), the oxygen concentrations available for the clinician to deliver become drastically limited.

Figure 2:
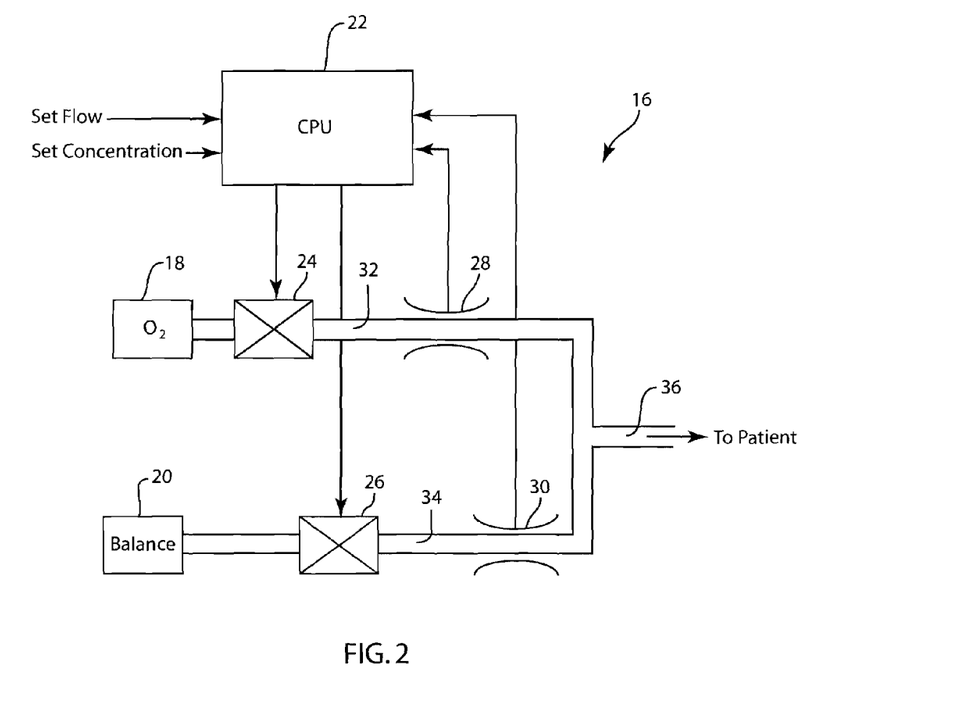
FIG. 2 depicts an embodiment of a medical gas mixing system.

FIG. 2 depicts an embodiment of a mixing system 16 that may be used as part of a larger gas delivery system (not depicted) for delivering medical gas and respiratory support to a patient. The mixing system 16 includes a source of oxygen 18 and a source of balance gas 20. These sources of medical gas may be movable cylinders, or may be a built in connection with the room in which the gas delivery system is located. The balance gas source 20 may be a source of medical gases such as air, nitrous oxide, nitrogen, helium, or any other suitable balance gases as recognized by one skilled in the art. It is also understood that the balance gas source 20 may include more than one source of balance gas as the medical gas delivered to the patient may be a mixture of any number of two or more medical gases. The mixing system 16 is controlled by a CPU 22 that receives a set flow rate for the total medical gas and a set oxygen concentration for the total medical gas delivered to the patient. Alternatively, the CPU 22 may receive the set flow rates of the medical gases directly, the concentration and total medical gas flow rates being implied or derived from the values of the set individual flows. The CPU 22 typically receives any set flow or concentration values from a clinician who is conducting the delivery of respiratory support to the patient.

The CPU 22, which may be a microprocessor or other programmable controller, achieves the set flow and concentration for the total medical gas by precisely controlling an oxygen flow valve 24 and a balance gas flow valve 26. The oxygen flow valve 24 controls the flow of oxygen from the oxygen source 18 into an oxygen conduit 32. A flow sensor 28 measures the flow of oxygen in the oxygen conduit 32 and relays this information back to the CPU 22 in a feed back loop to further facilitate the control of the flow of oxygen. Similarly, the balance gas flow valve 26 controls the flow of balance gas from the balance gas source 20 into the balance gas conduit 34. The flow of balance gas through the balance gas conduit 34 is monitored by a flow sensor 30 that relays the measured balance gas flow rate back to the CPU 22 in a balance gas feedback loop that enables the CPU 22 to more precisely control the flow of balance gas through the balance gas conduit 34.

The oxygen conduit 32 and the balance gas conduit 34 meet to form the medical gas conduit 36 that delivers the combined medical gas to the patient at the set flow rate and oxygen concentration.

Figure 3:
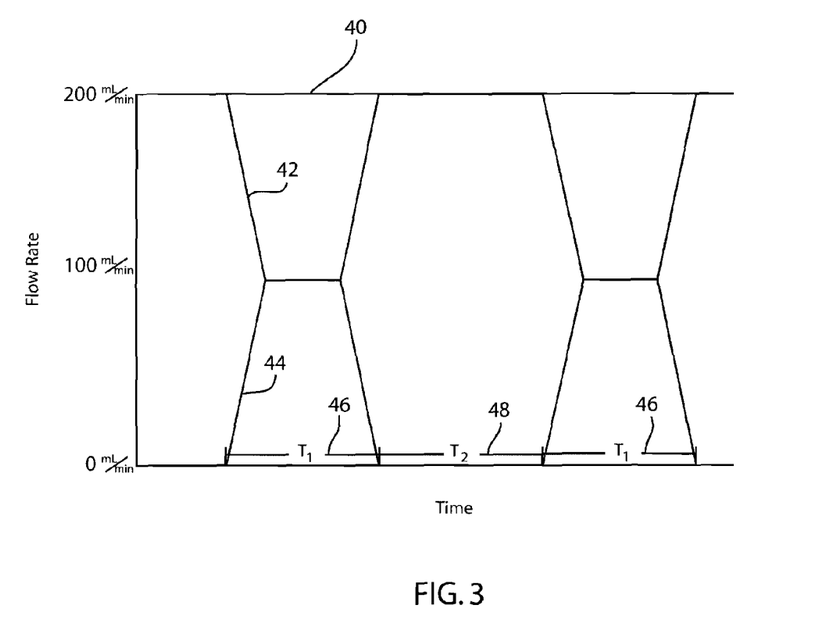
FIG. 3 is a graph depicting medical gas flow rates in accordance with an embodiment of the system and method.

As further disclosed herein, the improved control of the oxygen flow valve 24 and the balance gas flow valve 26 by the CPU 22 can greatly reduce the aforementioned resolution problem at low total medical gas flow rates. FIG. 3 depicts the flow of oxygen and balance gas as detected by the oxygen flow meter 28 and the balance gas flow meter 30 in a system as presently disclosed. Line 40 represents the total medical gas flow rate as set by the clinician. As indicated by line 40, the clinician has set the total medical gas flow rate at 200 ml/min to be delivered to the patient.

The flow rate of the balance gas 42 and the flow rate of oxygen 44 are separately controlled to achieve different levels of flow of the component medical gases. The flow of the medical gases is divided into a first time period (T1) 46 and a second time period (T2) 48. The CPU calculates the flow rates for each of the balance gas and oxygen gas as well as the durations of the T1 and T2 time intervals such that the average medical gas concentration over the entire time period of T1+T2 is equal to the oxygen concentration set by the clinician.

During the T1 time interval 46, it should be noted a flow of both balance gas 42 and oxygen 44 is present with the total flow of the balance gas 42 and oxygen 44 equaling the set total medical gas flow rate 40. During the T2 time interval 48 the balance gas 42 is provided at the set total medical gas flow rate 40. Therefore, the medical gas mixing system is constantly providing a flow of medical gas at the set flow rate.

In one embodiment, the T1 interval may be a fixed time interval, such as one second, that is combined with a variable T2 time interval. The one second T1 time interval may be due to the operational limitations of the flow sensor control loop response time. The time T1 is chosen such that the control loop stabilization time is only a small fraction of the time T1, and thus flow inaccuracies during the stabilization time do not contribute much to the error in the resulting output gas average concentration. The control loop stabilization time is the time that the gas mixing system requires after a change in a flow rate of a component gas to stabilize the flow rate of the component gas and achieve the optimal square wave delivery.

The initial onset or reduction of a flow of one or more of the component gasses may result in an over shoot or under shoot of the target flow rate followed by a series of oscillations. This introduces error into the system during the stabilization time, or the time it takes for the system to achieve the stable set flow rate.

In an alternative embodiment, the T1 and T2 time intervals may both be variable while the total time increment comprising the T1 and T2 time intervals (T1 and T2) remains at a fixed duration. In such an embodiment, the T1 and T2 time intervals would be calculated to optimize the desired concentration while ensuring that the average concentration is delivered over a set time interval.

Therefore, the average concentration of medical gas provided to the patient achieves the set medical gas concentration. While the component medical gases may be delivered in varying concentrations over time, the turbulence within the breathing circuit of the gas delivery system as well as a relatively short time duration for the T1 and T2 time intervals the resulting medical gas delivered to the patient is closely approximated by the average medical gas oxygen concentration over the T1 and T2 time intervals.

While FIG. 3 depicts the flow of oxygen and balance gas in a gas mixing system that is delivering a relatively low percentage of oxygen to the patient, thus requiring an average flow rate of oxygen less than the minimum 100 ml/min threshold, the flows of oxygen and balance gas may be modified such as to deliver a higher concentration of oxygen in the combined medical gas delivered to the patient.

In an embodiment presently disclosed, the desired average oxygen flow rate and the desired average balance gas flow rate are calculated from the set oxygen concentration and set total flow rate to be delivered to the patient. If the balance gas is a gas such as air that contains oxygen, then this oxygen flow is taken into account so that the average oxygen concentration of the resulting gas mixture is correct, given the oxygen component of the balance gas. If the calculated desired average flow through the oxygen flow sensor 28 is less than the 100 mL minimum threshold flow rate, then oxygen is the gas that is intermittently provided, and the balance gas is the gas that is always on. Conversely, if the calculated desired average flow through the balance gas flow sensor 30 is less than the 100 mL/min minimum threshold flow rate, then it is the balance gas that is intermittently provided, and oxygen is the gas that always on.

An embodiment that delivers a combined medical gas to the patient with a relatively high oxygen concentration, such that it is the balance gas whose desired average flow rate is less than the minimum flow, would differ in its output from that depicted in FIG. 3 in that the flow from the oxygen source would be constantly supplied, and the flow from the balance gas source would only be intermittently supplied. Thus the reversal of the medical gas flows as depicted in FIG. 3 would be used to achieve a combined medical gas concentration with a relatively high concentration of oxygen when the required average balance gas flow rate is below the minimum 100 ml/min flow rate.

Figure 4:
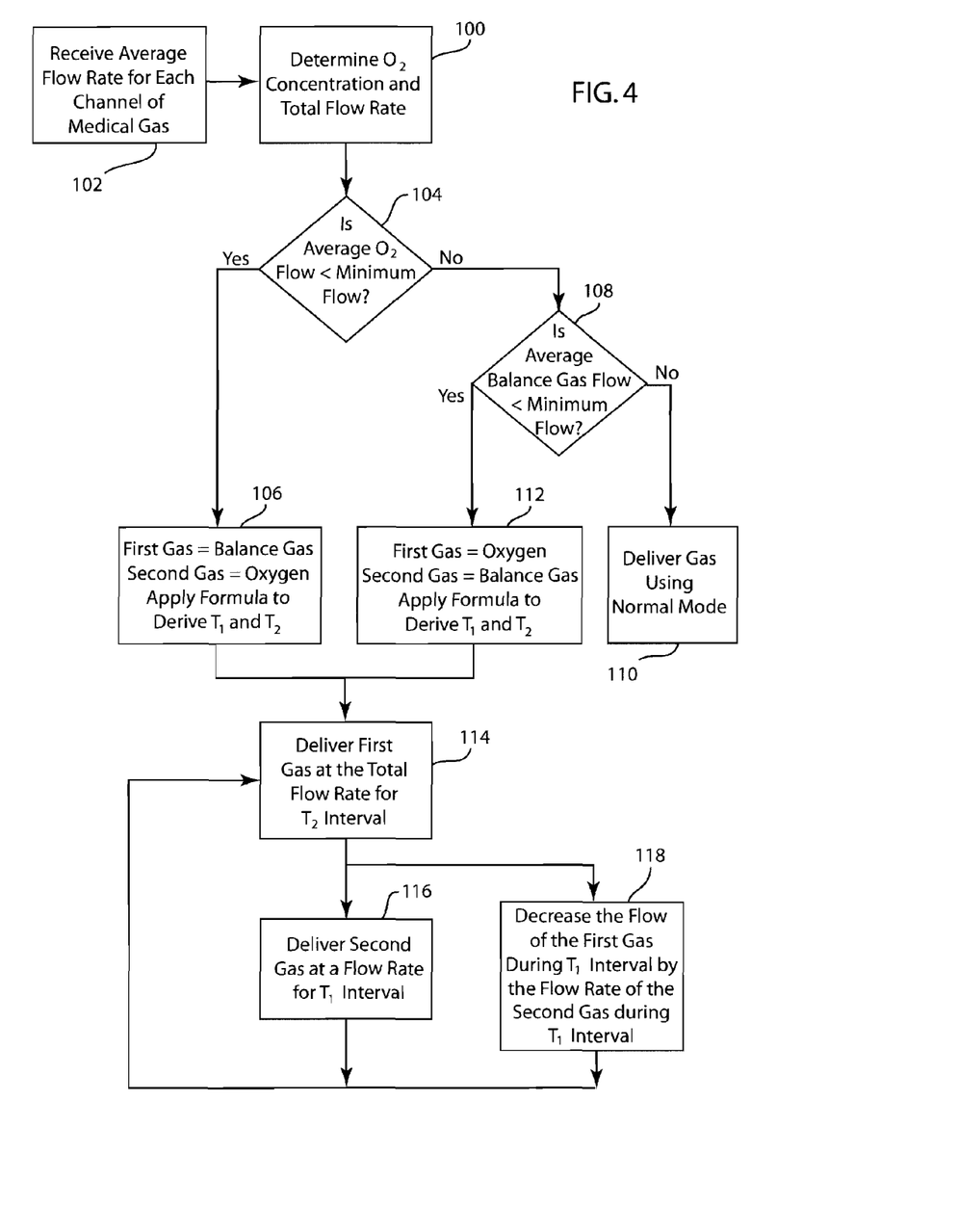
FIG. 4 is a flow chart depicting an embodiment of the method disclosed herein.

FIG. 4 depicts the steps of an embodiment of controlling the flow of medical gas into a ventilator mixing system such as depicted in FIG. 2 to produce to medical gas waveforms exemplified by FIG. 3.

First, the desired oxygen concentration and total medical gas flow rate to be delivered to the patient are determined in step 100. In one embodiment, the oxygen concentration and the total medical gas flow rate delivered to the patient are received from a clinician or other gas delivery system control source as part of an automated control system. In an alternative embodiment, the average flow rate for each channel of medical gas is received at step 102 and these values are used to calculate the total oxygen concentration and medical gas flow rate delivered to the patient. The average flow rate for each channel of medical gas may be received from a clinician input or other gas delivery system control source.

Next the average oxygen flow rate is compared to a threshold minimum flow rate in step 104. The average oxygen flow rate may be received in step 102 or may be calculated from the desired oxygen concentration and total medical gas flow rate from step 100. The threshold minimum flow rate is the minimum flow rate required for the gas flow sensors in the gas delivery system. If the average oxygen flow rate is less than the threshold minimum flow rate then the first gas is the balance gas and the second gas is the oxygen gas and a formula is applied to derive the T1 and T2 time intervals at step 106.

If, at step 104, the average oxygen flow rate is greater than the threshold minimum flow rate then at step 108 the average balance gas flow rate is compared to the threshold minimum flow rate. If the average balance gas flow rate is greater than the threshold minimum flow rate then both the average oxygen gas flow rate and the average balance gas flow rate are greater than the threshold minimum flow rate. The medical gases delivered using the normal operation of the gas delivery system at step 110 as the intermittent delivery is not needed. The normal gas delivery in step 110 may include delivering flows of medical gas at the determined average flow rates for each of the medical gases.

If, at step 108, the average balance gas flow rate is less than the threshold minimum flow rate, then, at step 112, the first gas is defined as oxygen and the second gas is defined as balance gas and a formula is applied to derive the T1 and T2 time intervals.

One such formula that may be applied to derive the T1 and T2 time intervals may use a fixed value for either the T1 or the T2 time interval and the formula is applied to derive the other of the two time intervals. In one embodiment the following equations may be used.

If T2 is defined:

$$T_1 = \frac{T_2 * secondgasflow}{(\min Flow - secondgasflow)}$$

where min Flow=threshold minimum Flow rate
If T1 is defined:

$$T_2 = \frac{T_1 x(\min Flow - secondgasflow)}{secondgasflow}$$

While these two equations or others reorganized by one skilled in the art may be used, in alternative embodiments the T1 and T2 time intervals may be alternatively constrained such as with a predefined sum of the T1 and T2 time intervals as opposed to predetermining one of the T1 or T2 time interval values.

Once the T1 and T2 have been determined, the first medical gas is delivered at the total flow rate for the T2 time interval at step 114. As discussed above, if the average oxygen flow is less than the threshold minimum flow then balance gas will be the first gas and if the average balance gas flow is less than the threshold minimum flow then oxygen will be the first gas. The first gas is delivered at the total flow rate for the entire T2 time interval. After the T2 time interval, the second gas (either the oxygen or balance gas was not delivered as the first gas) is delivered at a flow rate for the T1 time interval at step 116. Concurrent with the delivery of the second gas in step 116, the delivery of the first gas is decreased in step 118 by the same amount as the flow of the second gas delivered in step 112. Therefore, the total flow rate remains constant while the concentration of oxygen in the combined medical gas delivered to the patient is altered to achieve the desired oxygen concentration and total medical gas flow rate delivered to the patient.

In one embodiment, the delivery of the second gas at step 116 delivers the second gas at the threshold minimum flow rate. Consequently, at step 118 the flow of the first gas is decreased by the threshold minimum flow rate at which the second gas is delivered. In this embodiment the minimum flow rate for the second gas is used such that the delivery of the medical gas as close to the normal mode used in step 110 is achieved with the maximum period for the T1 and T2 time intervals. This may reduce strain on the system by reducing the number of cycles between the T1 and T2 time intervals resulting in opening and closing of the gas flow valves.

The modulated delivery of the oxygen and balance gas produces a combined medical gas with the desired oxygen concentration as received at step 100. Steps 114, 116, and 118 are repeated continuously during the delivery of medical gas at the required oxygen concentration and flow rate. If the clinician changes the desired oxygen concentration and/or total flow rate of medical gas at step 100, then the process repeats itself to control the delivery of medical gas at a new oxygen concentration or total medical gas flow rate.

If the oxygen gas is to be delivered at a flow rate below the threshold minimum flow rate for the oxygen flow sensor, then the oxygen source is pulsatedly added to the medical gas in the process as described above. To increase the oxygen concentration of the medical gas the width (time duration) of the oxygen pulse is lengthened to increase the average oxygen concentration in the medical gas. While the oxygen pulse is applied, the flow of balance gas is reduced by a similar amount such that a total flow of medical gas remains the same. If the desired flow rate of balance gas is less than the threshold minimum flow rate for the balance gas flow sensor, then the oxygen is continuously provided to the patient while pulses of balance gas are intermittently added to decrease the average oxygen concentration of the medical gas. The oxygen concentration can then be further reduced by lengthening the width (time duration) of the balance gas pulses. The pulses of medical gas (oxygen or balance) may be set to be at least at the threshold minimum flow rate. Alternative embodiments may deliver the pulses of medical gas at a rate greater than the threshold minimum flow rate. Thus, an improved resolution and concentration range for an oxygen component of medical gas to be delivered to a patient may be achieved while only delivering medical gas at a flow rate greater or equal to the minimum medical gas flow rate.

In one embodiment, the aforementioned control system and method are implemented only when either the oxygen or balance gas is desired to be delivered at an average flow rate less than the threshold minimum flow rate necessary for the flow sensors in the gas delivery system. Such an embodiment may only require the improved resolution of oxygen concentration when medical gas is delivered at low flow rates, and therefore the aforementioned system and method may not be implemented during the delivery of medical gas at flow rates that allow for sufficient resolution by conventional methods. One reason for such a hybrid implementation of medical gas concentration control may be the increased wear on the medical gas source flow valves experienced in embodiments disclosed herein from the required repetitive opening and closing of the valves, as opposed to the fixed valve opening used in conventional systems.

In an embodiment of the system and method as disclosed herein, sometimes it is clinically desirable to deliver a hypoxic mixture of medical gas. In these embodiments, oxygen may be replaced by air and combined with a flow of another balance gas. In such cases, it is likely that the balance gas will be delivered intermittently as to maintain a minimum level of oxygen being delivered to the patient.

It should be noted that some embodiments of the system and method as disclosed herein may be implemented solely through the use of the computer in that a computer may be associated with a computer readable medium that is configured with computer readable code such that a computer may read the computer readable code from the computer readable medium and execute the controls of the gas delivery system as defined by the computer readable code. Such embodiments as disclosed herein may achieve the technical effect of improving the concentration range and resolution of a medical gas delivered to a patient by a mechanical ventilator.

This written description uses examples to disclose the invention including the best mode, and also to enable any person skilled in the art to make and use the invention. The patentable scope is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

Various alternatives and embodiments are contemplated as being with in the scope of the following claims, particularly pointing out and distinctly claiming the subject matter regarded as the invention.

What is claimed is:

1. A method of controlling the provision of a first medical gas and a second medical gas to a patient, wherein one of the first and second medical gases comprises oxygen, the method including:
    defining a desired oxygen concentration to be delivered to the patient;
    defining a desired total medical gas flow rate to be delivered to the patient;
    controlling a first valve to deliver a first flow of the first medical gas at the desired total medical gas flow rate for a first time interval;
    controlling a second valve to intermittently deliver a second flow of the second medical gas for a second time interval while decreasing the first flow of the first medical gas by an amount commensurate to the second flow of the second medical gas for the second time interval such that an average oxygen concentration delivered to the patient across the first and second time intervals equals the desired oxygen concentration.

2. The method of claim 1 wherein the decreased first flow of the first medical gas is concurrent to the delivery of the second medical gas such that the desired total medical gas flow rate is maintained.

3. The method of claim 2 wherein the second flow of the second medical gas is equal to a minimum flow rate as set by the flow sensing element.

4. The method of claim 1 wherein the desired oxygen concentration to be delivered to the patient and the desired total medical gas flow rate to be delivered to the patient are defined by receiving the definitions from a clinician input.

5. The method of claim 1 further comprising:
receiving a definition of an average flow rate of oxygen; and
receiving a definition of an average flow rate of at least one balance gas.

6. The method of claim 5 wherein the desired oxygen concentration to be delivered to the patient and the desired total medical gas flow rate to be delivered to the patient are defined by deriving them from the average flow rates of oxygen and at least one balance gas.

7. The method of claim 5 further comprising the steps of:
comparing the average flow rate of oxygen to a predetermined threshold minimum flow rate;
wherein if the average flow rate of oxygen is below the threshold minimum flow rate, defining the first medical gas as the at least one balance gas and the second medical gas as oxygen.

8. The method of claim 7 flintier comprising the steps of:
comparing the average flow rate of each balance gas to a predetermined threshold minimum flow rate;
wherein if the average flow rate of the balance gas is below the threshold minimum flow rate, defining the first medical gas as oxygen and the second medical gas as the at least one balance gas.

9. The method of claim 8 wherein if the average flow rate of oxygen and the balance as are both above the predetermined threshold minimum flow rate, delivering the oxygen and the balance gas to the patient at the average flow rate of oxygen and the average flow rate of at least one balance gas.

10. The method of claim 1 wherein the average oxygen concentration delivered to the patient is determined by calculating the average flow of the first and second medical gasses over the time of the first flow of first medical gas and the second flow of second medical gas.

11. A method of controlling the provision of oxygen gas and balance gas to a patient when one of an oxygen gas average flow rate or balance gas average flow rate is below a minimum operational flow rate required by at least one flow sensor in a medical gas mixing system, the method including:
defining a target total medical gas flow rate to be delivered to the patient;
defining a target average oxygen concentration to be delivered to the patient.;
determining the oxygen gas average flow rate from the target total medical gas flow rate and the target average oxygen concentration;
determining the balance gas average flow rate from the target total medical gas flow rate and target average oxygen concentration;
comparing the oxygen gas average flow rate and the balance gas average flow rate to the at least one flow sensor minimum operational flow rate;
defining the oxygen gas or the balance gas with the average flow rate at or above the threshold minimum flow rate as the first gas;
defining the oxygen gas or the balance gas with the average flow rate below the threshold minimum flow rate as the second gas;
delivering a first flow of the first gas at the target total medical gas flow rate for a first time interval;
delivering a second flow of the second gas at a second flow rate for a second time interval; and
commensurate with the delivery of the second flow of the second gas, decreasing the first flow of the first gas by the second flow rate for the second time interval;
wherein the target total medical gas flow rate is maintained throughout the first and second time intervals, and the delivery of the first gas and the second gas across the first and second time intervals achieves the average oxygen concentration to be delivered to the patient.

12. The method of claim 11, further comprising calculating at least one of the second flow rate and the second time interval such that the delivery of the first and second gases across the first and second time intervals achieves the average oxygen concentration to be delivered to the patient.

13. The method of claim 12 wherein the oxygen gas average flow rate is below an oxygen flow sensor minimum operational flow rate and the first gas is balance gas and the second gas is oxygen gas.

14. The method of claim 12 wherein the balance gas average flow rate is below a balance gas flow sensor minimum operational flow rate and the first gas is oxygen gas and the second gas is balance gas.

15. A gas delivery system for delivering at least first medical gas and a second medical gas to a patient at a target total flow rate and a target average oxygen concentration, the system comprising:
a first source of a first medical gas;
a first flow valve associated with the first source to regulate the flow of the first medical gas;
a second source of a second medical gas;
a second flow valve associated with the second source to regulate the flow of the second medical gas; and
a controller communicatively connected to the first and second flow valves, the controller controlling the first or second flow valve to produce a first flow of the first or second medical gas at the determined flow rate for a first time period and intermittently controlling the other of the first or second flow valves to produce a second flow of the other of the first or second medical gas, while controlling the first or second flow valve to reduce the first flow of medical gas to maintain the target total flow rate for a second time period, to achieve the target average oxygen concentration between the flows of the first and second medical gases over the combined first and second time periods.

16. The system of claim 15 further comprising:
a first flow sensor associated with the first source and the first flow valve and communicatively connected to the controller, the first flow sensor monitoring the flow of the first medical gas; and
a second flow sensor associated with the second source and the second flow valve and communicatively connected to the controller, the first flow sensor monitoring the flow of the second medical gas;
wherein the first flow sensor and the second flow sensor have a threshold minimum flow rate required to properly operate.

17. The system of claim 16 wherein the controller receives a definition of an average flow rate for the first medical gas and an average flow rate for the second medical gas and compares the average flow rates for the first medical gas and the second medical gas to the threshold minimum flow rate.

18. The system of claim 17 wherein the first medical gas flow rate is below the threshold minimum flow rate and the second medical gas flow rate is at or above the threshold minimum flow rate, and the second flow valve is operated to produce the first flow of the second medical gas and the first flow valve is operated to produce the second flow of the first medical gas.

19. The system of claim 17 wherein the first medical gas flow rate is at or above the threshold minimum flow rate and the second medical was flow rate is below the threshold minimum flow rate, the first flow valve is operated to produce the first flow of the first medical gas and the second flow valve is operated to produce the second flow of the second medical gas.

20. The system of claim 17 wherein either the first medical gas or the second medical gas is oxygen.

* * * * *